(12) United States Patent
Greivenkamp, Jr. et al.

(10) Patent No.: US 11,213,198 B2
(45) Date of Patent: Jan. 4, 2022

(54) SYSTEM AND METHOD FOR THE RAPID MEASUREMENT OF THE VISUAL CONTRAST SENSITIVITY FUNCTION

(71) Applicant: Johnson & Johnson Vision Care, Inc., Jacksonville, FL (US)

(72) Inventors: John E. Greivenkamp, Jr., Tucson, AZ (US); Gregory A. Williby, St. Johns, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 143 days.

(21) Appl. No.: 16/444,352

(22) Filed: Jun. 18, 2019

(65) Prior Publication Data

US 2019/0298165 A1    Oct. 3, 2019

Related U.S. Application Data

(62) Division of application No. 15/078,001, filed on Mar. 23, 2016, now Pat. No. 10,362,934.

(51) Int. Cl.
*A61B 3/02* (2006.01)
*A61B 3/00* (2006.01)
*A61B 3/032* (2006.01)

(52) U.S. Cl.
CPC ............ *A61B 3/022* (2013.01); *A61B 3/0025* (2013.01); *A61B 3/0033* (2013.01); *A61B 3/0041* (2013.01); *A61B 3/0083* (2013.01); *A61B 3/032* (2013.01); *A61B 2562/185* (2013.01)

(58) Field of Classification Search
CPC ... A61B 3/0025; A61B 3/0041; A61B 3/0033; A61B 3/0083; A61B 3/022; A61B 3/032; A61B 2562/185
See application file for complete search history.

(56) References Cited

U.S. PATENT DOCUMENTS

| | | | |
|---|---|---|---|
| 4,365,873 A | 12/1982 | Ginsburg |
| 5,694,199 A | 12/1997 | Rodriguez |
| 7,311,400 B2 | 12/2007 | Wakil |
| 7,938,538 B2 | 5/2011 | Lu |
| 8,454,165 B2 | 6/2013 | Duffy |
| 2003/0174284 A1 | 9/2003 | Stewart |
| 2004/0076942 A1 | 4/2004 | O'Neil |
| 2005/0012900 A1 | 1/2005 | Holladay |

(Continued)

FOREIGN PATENT DOCUMENTS

| | | |
|---|---|---|
| CN | 104545785 A | 4/2015 |
| GB | 2514529 A | 1/2013 |

(Continued)

OTHER PUBLICATIONS

Pelli, Denis G. et al, Measuring contrast sensitivity, Vision Res., Sep. 20, 2013; 90: 10-14.

(Continued)

*Primary Examiner* — Jack Dinh (57) ABSTRACT

A computer, a high resolution monitor and a patient interface is utilized to implement a visual contrast sensitivity function measurement test. More specifically, a computerized video system is configured to implement a tilted-grating forced choice contrast sensitivity function test. The invention utilizes known measurement methods for the visual contrast sensitivity function and automates their use by computerizing the system and couples it with a patient-interactive user interface in order to produce an accurate quantitative result.

7 Claims, 9 Drawing Sheets

(56) References Cited

U.S. PATENT DOCUMENTS

| | | |
|---|---|---|
| 2006/0023163 A1 | 2/2006 | Foster |
| 2011/0007267 A1 | 1/2011 | Erickson |
| 2013/0100410 A1 | 4/2013 | Liang |
| 2015/0022782 A1 | 1/2015 | Hofeldt |
| 2015/0070650 A1 | 3/2015 | Seriani |

FOREIGN PATENT DOCUMENTS

| | | |
|---|---|---|
| RU | 2401051 C1 | 10/2010 |
| WO | WO2006047369 A2 | 5/2006 |

OTHER PUBLICATIONS

Hong YT[1] et al., Contrast sensitivity measurement with 2 contrast sensitivity tests in normal eyes and eyes with cataract, J Cataract Refract Surg. Apr. 2010;36(4):547-52.

Richman MD, Jesse et al., Contrast sensitivity basics and a critique of currently available tests, Journal of Cataract & Refractive Surgery, vol. 39, Issue 7, Jul. 2013, pp. 1100-1106.

Shapley, R. et al., Spatial Frequency Analysis in the Visual System, Annual Review of Neuroscience, vol. 8: 547-581 (Volume publication date Mar. 1985).

Treutwein, Bernhard, Adaptive psychophysical procedures, Vision Research, vol. 35, Issue 17, Sep. 1995, pp. 2503-2522.

Benda et al, "From response to stimulus: adaptive sampling in sensory physiology", Current Opinion in Neurobiology, London, GB, vol. 17, No. 4, Aug. 1, 2007, pp. 430-436, XP022289652, ISSN: 0959-4388.

EP Search Report for corresponding EPA No. 17162380.4 dated Sep. 18, 2017.

Singapore Search Report from corresponding SG Application No. 10201702280Y dated Nov. 22, 2017.

Russian Search Report from corresponding RU Application No. 2017109303 dated Apr. 26, 2018.

Manuel Rodriguez-Vallejo et al. Designing a new test for contrast sensitivity function measurement with iPad, Journal of Optometry, vol. 8, Issue 2, 2015, pp. 101-108.

Campbell F. W. & Robson J. G., Application of Fourier analysis to the visibility of gratings. *The Journal of physiology*, Aug. 1, 1968, vol. 197, No. 3, pp. 551-566. Whole document.

Moseley M. J. & Hill A. R., Contrast sensitivity testing in clinical practice. *British Journal of Ophthalmology*, Oct. 30, 1994, vol. 78, pp. 795-797. Whole document.

Woods R. L. & Wood J. M., The role of contrast sensitivity charts and contrast letter charts in clinical practice. *Clinical and Experimental Optometry*, Mar. 31, 1995, vol. 78, No. 2, pp. 43-57. Whole document.

SYSTEM AND METHOD FOR THE RAPID MEASUREMENT OF THE VISUAL CONTRAST SENSITIVITY FUNCTION

CROSS REFERENCE TO RELATED APPLICATION

The present application is a divisional application of U.S. patent application Ser. No. 15/078,001 filed on Mar. 23, 2016.

BACKGROUND OF THE INVENTION

1. Field of the Invention

The present invention relates to a computerized visual contrast sensitivity function measurement system, and more particularly to a computerized video system configured to implement a tilted-grating, forced choice contrast sensitivity function test. Even more particularly, the present invention utilizes known measurement methods for the visual contrast sensitivity function and automates their use by computerizing the system and couples it with a patient-interactive user interface that records the shape of a results curve producing an accurate quantitative result.

2. Discussion of the Related Art

Simply speaking, contrast is a measure of the amount of lightness or darkness an object has relative to its background, or in other words, it is the difference in luminance that makes an object distinguishable. For example, a black letter on a white background has more contrast than a black letter on a gray background. The contrast threshold is the smallest difference of the lightness and darkness between an object being viewed and its background that can be distinguished by a viewer. Contrast sensitivity is the inverse of the contrast threshold which defines the threshold between the visible and the invisible, and thus any reduction in contrast sensitivity may impair daily activities, including reading, utilizing tools, driving, and simply finding objects. There are diseases that may cause a loss of contrast sensitivity as well as improperly designed optics, including spectacles and contact lenses.

An object's size, or more specifically, the angle it subtends in space, influences how much contrast is required to differentiate an object from its background. The size of an object may be depicted by alternating lines of light and dark with an appropriate spacing occupying a specific visual angle. The number of light and dark lines within the specific visual angle is referred to as the spatial frequency. Densely packed lines represent a high spatial frequency while sparsely packed lines represent a low spatial frequency. The relationship between contrast sensitivity and spatial frequency is known as the contrast sensitivity function. Determining an individual's contrast sensitivity function may provide a valuable clinical adjunct to standard visual acuity tests or measurements. More specifically, whereas acuity is a test of visual resolution or detection and the maximum frequency detectable, the contrast sensitivity function tests performance across a range of spectral frequencies and this range can be correlated to subjective visual satisfaction.

It is generally accepted that contrast sensitivity function (CSF) measurements are an important and informative method for assessment of the human visual system. However, these measurements are only infrequently made in research environments and rarely in the clinical setting. The primary reason it is rarely utilized is the length of time required to complete an effective measurement. It is simply impractical as a routine test. In addition, the length of time required for the measurement may lead to measurement inaccuracies due to subject fatigue.

The traditional CSF test employs a series of images or test charts with various spatial frequencies and contrast levels. Typically, a large number of these individual charts are shown to the subject who must make a forced choice as to the presence of a pattern. From these choices, and the long process, the CSF can be determined; however, subject fatigue is often a factor in accuracy as set forth above.

The basic components of a two alternative forced choice test or task includes two alternative choices, for example, two possible visual stimuli, a delay interval to allow a response/choice, and a response indicating a choice of one of the two possible stimuli. For contrast sensitivity function testing, the preferred stimuli are a series of targets consisting of sinusoidal gratings of differing spatial frequency and contrast. To provide a detection method, the gratings are tilted either slightly to the left or to the right or are vertical. For each target the subject must respond with the orientation, even if it is just a guess. The CSF is determined when the threshold between "seeing" and "not-seeing" is determined to some level of precision for each spatial frequency of interest.

Figure 1A:
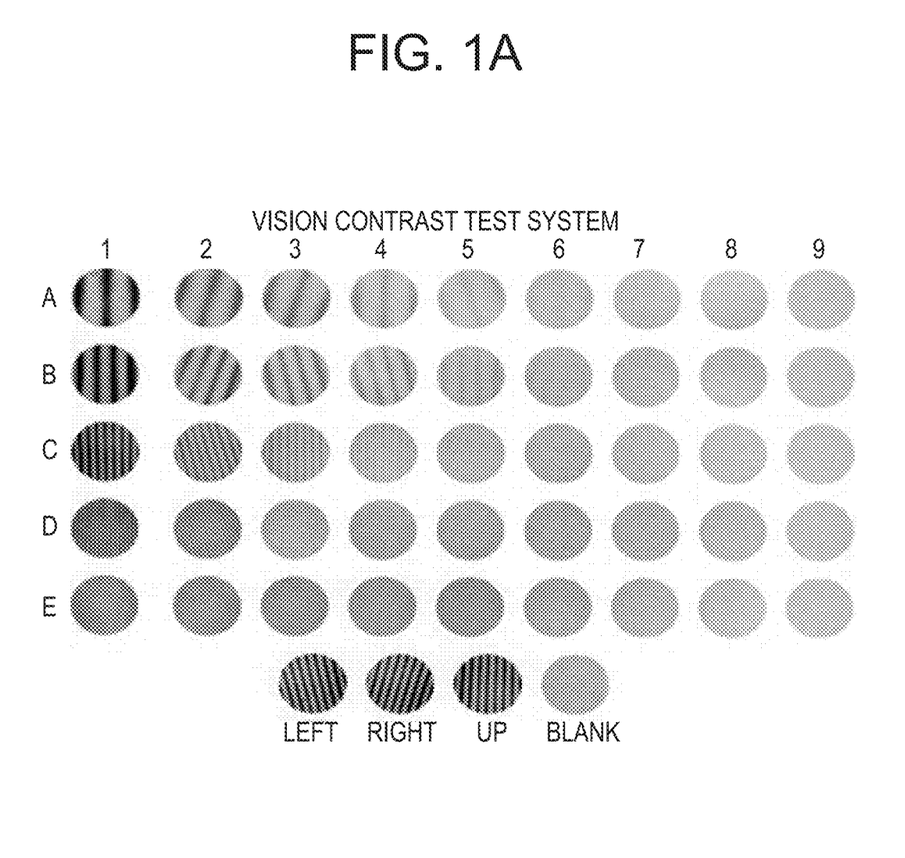
FIGS. 1A and 1B are examples of test charts with tilted gratings that are currently utilized in contrast sensitivity function testing.
Figure 1B:
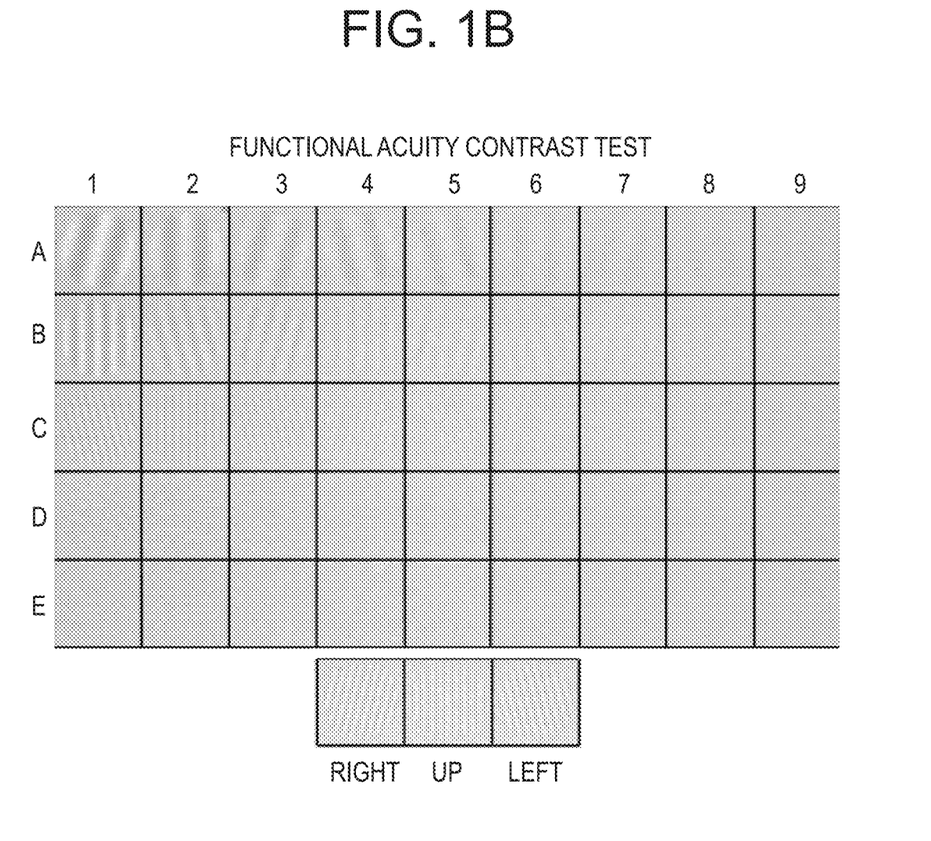

The vision Contrast Test System (Vistech) and the Functional Acuity Test System (Vision Science Research Corporation) are commercially available charts produced to implement this test. Examples of these charts are shown in FIGS. 1A and 1B respectively. However, only a small number of charts are used and while the subject must respond for each patch, the patches are presented in order and not as a single test. The presence of other patches as well as spatial variations, such as in illumination, can influence the result.

A variety of other chart-based tests have been demonstrated and a good review can be found by Richmman, Spaeth and Wirostko ("Contrast sensitivity basics and a critique of currently available tests," J Cataract Refract Surg 2013; 39:1100-1106). The tests described generally present the subject with two or more patches and the subject must determine which contains the pattern. Since a fixed series of patterns, such as illustrated in FIGS. 1A and 1B are used, the test is subject to the influences of learning. Some of these tests have also been implemented with a video apparatus.

Accordingly, there exists a need for a patient-interactive visual contrast sensitivity function measurement system and method that can rapidly assess visual performance, increase the accuracy of the test and produce a quantitative result that may be utilized to design better optics for patients.

SUMMARY OF THE INVENTION

The utilization and implementation of a known qualitative measurement method for the visual contrast sensitivity function by computerizing and coupling it with a patient-interactive user interface that records the shape of a results curve thereby producing a quantitative result of the present invention overcome the disadvantages associated with the prior art as briefly described above.

In accordance with a first aspect, the present invention is directed to a method for implementing a tilted-grating, forced choice contrast sensitivity function test. The method comprising the steps of presenting a patient with a first series of randomized test chart sets with two or more choices per set on a high resolution display as a video and covering a first range of frequencies and contrasts, having the patient select a response from the two or more choices, recording if the response is correct or incorrect, and providing the patient with additional choices until the first series of test charts are complete and a contrast sensitivity function is generated to a desired precision based upon an analysis of the responses, analyzing the responses utilizing statistical methods, repeating the method until a desired ophthalmic resolution is obtained as determined by an adaptive algorithm, and storing and plotting the contrast sensitivity function to provide an accurate quantitative result for the contrast sensitivity function.

In accordance with another aspect, the present invention is directed to a method for implementing a tilted-grating, forced choice contrast sensitivity function test. The method comprising the steps of presenting a patient with a first series of randomized test chart sets with two or more choices per set on a high resolution display as a video and covering a first range of frequencies and contrasts, having the patient select a response from the two or more choices, recording if the response is correct or incorrect, recording the time the patient utilized in making the response, and providing the patient with additional choices until the first series of test charts are complete, analyzing the responses to determine a first contrast sensitivity function, presenting the patient with additional series of randomized test chart sets with two or more choices per set on a high resolution display as a video and covering a at least one of a second range of frequencies and contrasts in smaller increments than the first range of frequencies and contrasts, a change in spatial frequencies, a change in contrast, a change in spatial frequencies and contrast and continue until a contrast sensitivity function is generated to a desired precision, having the patient select a response from the two or more choices, recording if the response is correct or incorrect, recording the time the patient utilized in making the response, and providing the patient with additional choices until the second series of test charts are complete, analyzing the responses utilizing statistical methods, repeating the method until a desired ophthalmic resolution is obtained as determined by an adaptive algorithm, and storing and plotting the contrast sensitivity function to provide an accurate quantitative result for the contrast sensitivity function.

In accordance with still another aspect, the present invention is directed to a computerized video system configured to implement a tilted-grating forced choice contrast sensitivity function test. The system comprising a computer and associated memory for storing multiple series of test charts with two or more choices per set and covering multiple ranges of frequencies and contrasts in various increments to be displayed as a video, the computer implementing an algorithm that generates the video of the test charts in a randomized manner, records choices made by a patient, records the time to make a choice, changes the frequency and contrast based upon analysis of the data collected for a highly refined and accurate test, and outputs a quantitative result of the contrast sensitivity function for the patient, a high resolution display for displaying the multiple series of test charts, a means for ensuring that a patient is properly positioned the desired distance from the high resolution display for the test, and a patient interface configured to allow the patient to select a response from the two or more choices.

Figure 2:
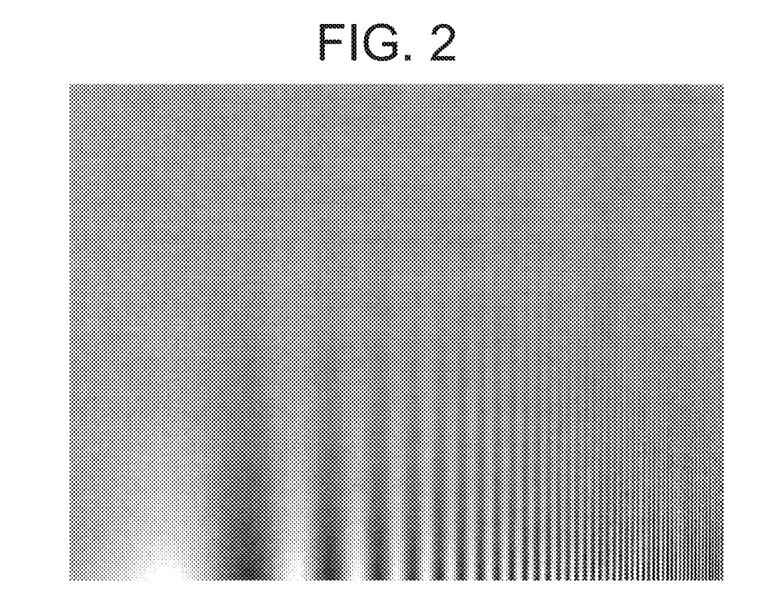
FIG. 2 is a Campbell-Robson contrast sensitivity function chart.

It is generally accepted that contrast sensitivity function or CSF measurements are an important and informative method for assessment of the human visual system. Loss of contrast sensitivity may impair any number of daily activities, for example, driving, as well as be an indicator of certain diseases. Accordingly, accurate CSF measurements may be particularly beneficial. It is also well known that a qualitative measurement of CSF may be determined from a Campbell-Robson CSF chart (FIG. 2). This single chart has a variable spatial frequency (cycles/degree) along the horizontal axis and a variable contrast sensitivity along the vertical axis. With this chart it is possible to visualize your CSF by merely noting where the pattern appears to disappear.

The present invention utilizes the speed, flexibility and efficiency of a computerized video system to fully implement a tilted-grating, forced choice test. A large number of test patterns may be generated and stored in the memory of a computer system. Each test pattern includes a patch with a sinusoidal pattern of a single spatial frequency with some level of contrast. The pattern is either tilted to the right, tilted to the left of not tilted at all, i.e. vertical. In addition, the spatial frequency contained in a specific test pattern is constant. In other exemplary embodiments, there may be only two choices, e.g. tilted left or right, which may prove to be more beneficial than a three choice test. The patterns are presented one at a time to the patient on a high resolution display at a prescribed viewing distance. The patient will then have three (or two as the case may be) buttons to push; namely, one corresponding to each orientation, and must provide a response, even if it is a guess. The flexibility afforded by implementing this test on a computer is that it allows for a randomized use of test patterns seamlessly in the same test setting to counter any impact due to the patient's memory of the patterns. Once a button is pushed, a different pattern is presented. It is important to note that the buttons can be part of the user interface or simply part of a touch screen display depending on how the test is configured, for example, near or distance visual testing.

The present invention provides for accurate visual contrast sensitivity function testing. The test is easily implemented, engaging for the patient, provides for quantitative measurement rather than simply qualitative measurement, and fast, thereby positively impacting the patient experience.

BRIEF DESCRIPTION OF THE DRAWINGS

The foregoing and other features and advantages of the invention will be apparent from the following, more particular description of preferred embodiments of the invention, as illustrated in the accompanying drawings.

DETAILED DESCRIPTION OF THE PREFERRED EMBODIMENTS

It is generally accepted that contrast sensitivity function or CSF measurements are an important and informative method for assessment of the human visual system. It is also well known that a qualitative measurement of CSF may be determined from a Campbell-Robson CSF chart as illustrated in FIG. 2. This single chart has a variable spatial frequency (cycles/degree) along the horizontal axis and a variable contrast sensitivity along the vertical axis. As illustrated, the spatial frequency increases as one moves from left to right and the contrast sensitivity decreases as one moves up along the vertical axis. With this chart it is possible to visualize your CSF by merely noting where the pattern appears to disappear. The curve usually has the shape of an upside-down U as indicated by trace 300 in FIG. 3.

In one exemplary embodiment, the present invention automates the use of the Campbell-Robson chart through the use of a computer and a high resolution digital display in conjunction with a patient-interactive user interface that records the shape of the curve. A rapid measurement is made by viewing just a few charts, as it may be necessary to flip the chart in different orientations as is explained in greater detail subsequently.

The Campbell-Robson chart is preferably displayed with sufficient dynamic range to preserve all of the information contained within the chart. A high-end radiographic monitor with a dynamic range of 10 to 12 bits is preferred. It is important to understand that for every increase of 1 bit, the contrast resolution of the monitor is doubled. The monitor should be shielded to prevent ambient light from influencing the measurements by control of the test environment or other suitable means such as being enclosed in a box. The subject or patient views the monitor at a prescribed test distance, or alternatively a viewing system comprising two eyepieces may be utilized to image the monitor to the desired viewing distance for the subject or patient. In an alternative exemplary embodiment, two monitors may be utilized in conjunction with a haptoscope. This would allow for tests on whether or not binocular vision is achieved through summing the images from each eye or blocking unwanted features from each eye.

Figure 3:
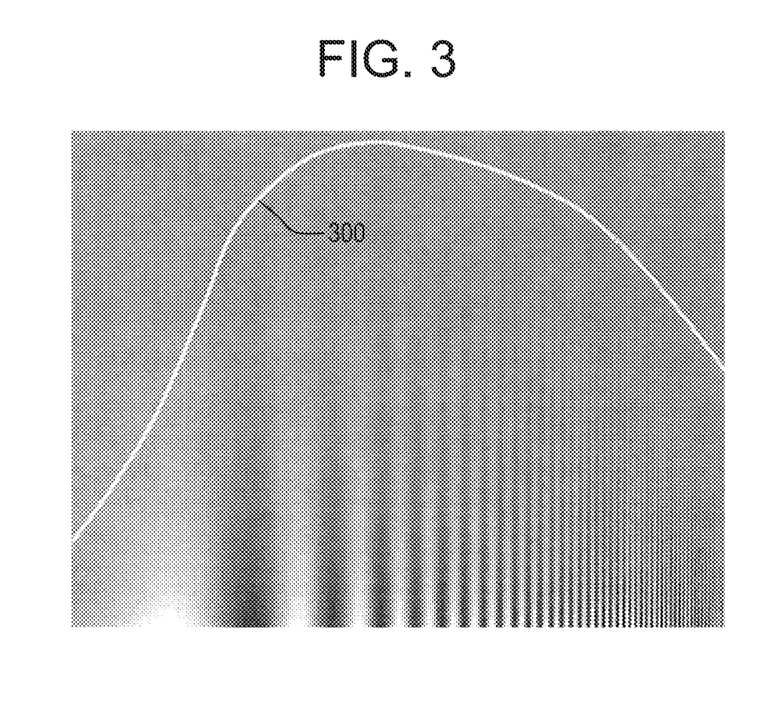
FIG. 3 is a Campbell-Robson contrast sensitivity function chart with a trace of a contrast sensitivity function.
Figure 4:
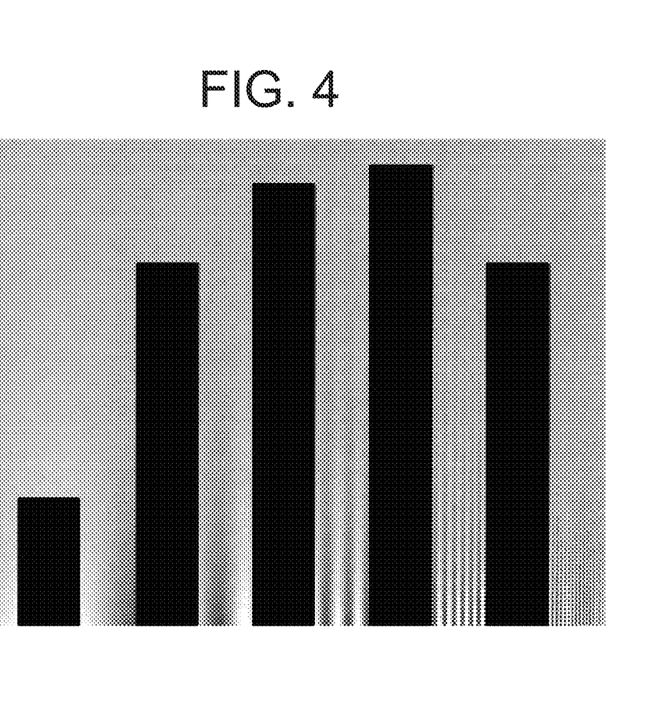
FIG. 4 is a series of user generated bars overlying different spatial frequencies of a Campbell-Robson contrast sensitivity function chart with the bars originating from the bottom of the chart.
Figure 5:
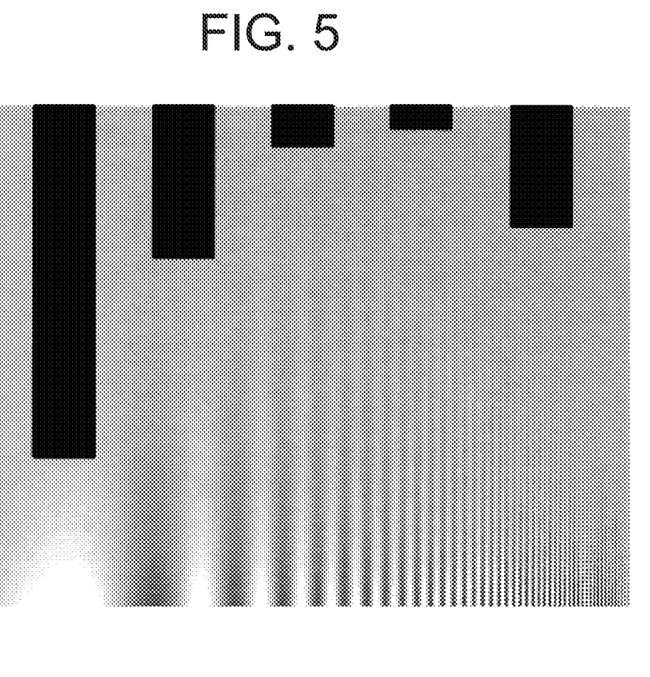
FIG. 5 is a series of user generated bars overlying different spatial frequencies of a Campbell-Robson contrast sensitivity function chart with the bars originating from the top of the chart.

Any suitable means may be utilized for the patient-interactive user interface. For example, a mouse may be utilized by the patient to create the curve 300 as illustrated in FIG. 3. Alternative exemplary embodiments may make use of a moving bar system that the patient stops at the appropriate time. The bars may originate from the top or the bottom of the chart. In FIG. 4, the bars to measure at specific spatial frequencies originate from the bottom of the chart, while the bars in FIG. 5 originate from the top of the chart. In yet another alternate exemplary embodiment, an eye tracking or an eye gaze tracking system may also be utilized so that the patient may trace out the curve with their eyes by simply gazing at different points. In still another exemplary embodiment, a touch screen with or without a stylus, may be utilized to trace the CSF curve.

Figure 6:
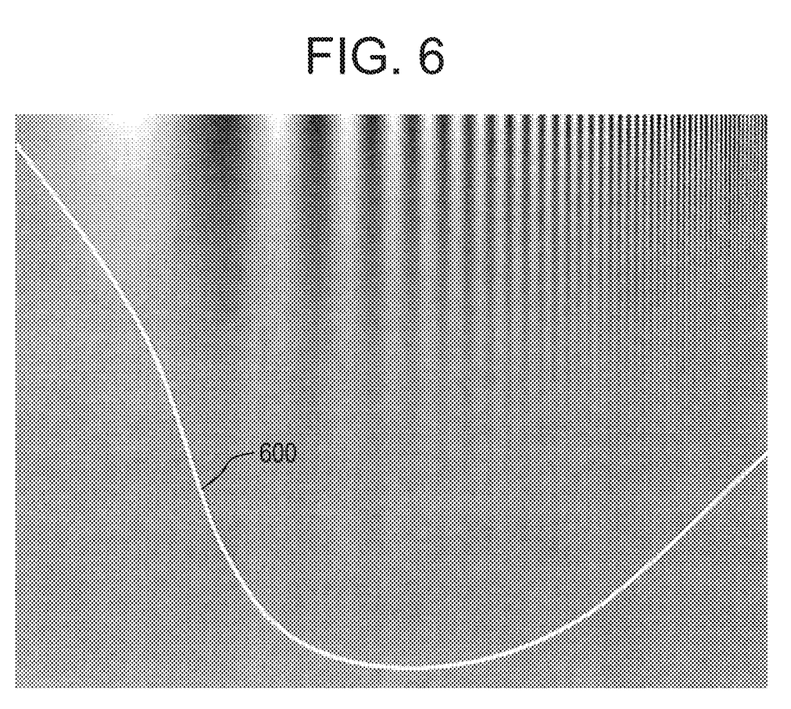
FIG. 6 is an inverted Campbell-Robson contrast sensitivity function chart with a trace of a contrast sensitivity function.
Figure 7:
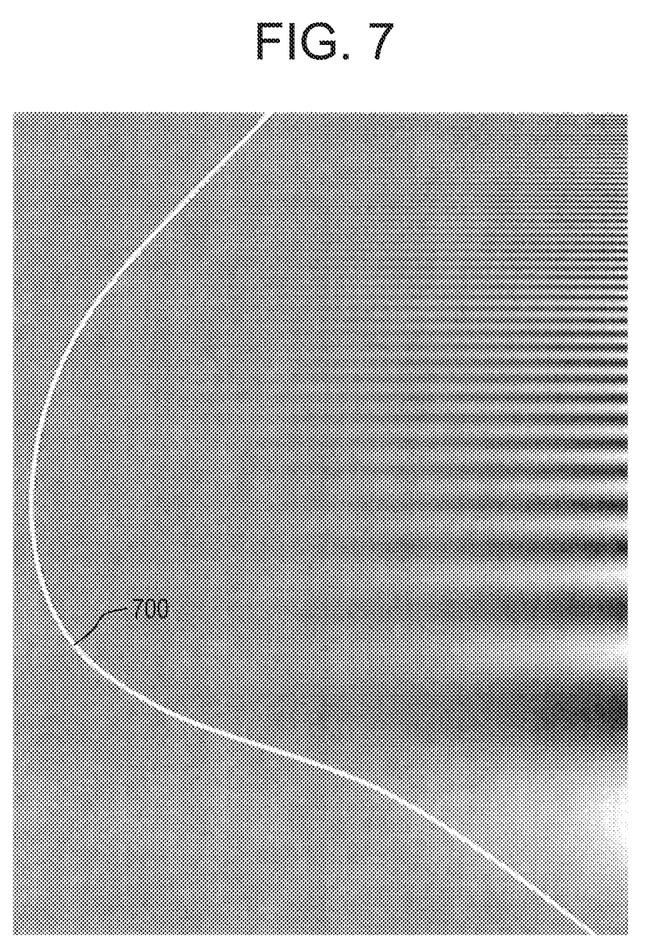
FIG. 7 is a rotated Campbell-Robson contrast sensitivity function chart with a trace of a contrast sensitivity function.

To remove bias, the Campbell-Robson charts may be presented in different orientations. For example, FIG. 6 illustrates an inverted CSF chart with a drawn curve 600, while FIG. 7 illustrates a CSF chart rotated ninety (90) degrees with a drawn curve 700. The situations illustrated in FIGS. 3 and 6 both measure the same horizontal CSF, while the rotation in FIG. 7 measures the vertical CSF of the visual system, and provides a fuller evaluation of visual performance. It should be noted that this vertical CSF measurement is rarely if ever measured. Even with additional orientations, only several charts will need to be evaluated. In addition, charts with either a black surround or a white surround may be presented. The white surround allows for the effects of scatter light within the eye on the contrast sensitivity function. Furthermore, the illumination of the surrounding white pattern may be adjusted to increase the impact of scatter. This is somewhat analogous to watching a movie in a dark theater or in a theater with the lights on. The same stimulus is provided, but the viewing quality is quite different. More particularly, in technical terms, noise is added to the signal, making signal detection more difficult. In other words, the stimulus changes from signal to signal plus noise.

The tests described based upon using the full Campbell-Robson chart will provide quantitative measurement of the CSF; however, they are not forced choice tests and may be unlikely to provide the level of accuracy required for clinical evaluation and differentiation. However, another option may include utilizing the Campbell-Robson test as a pre-test to identify the approximate CSF curve and then use the forced choice test to get accurate quantitative measurements as explained in greater detail subsequently.

Figure 9:
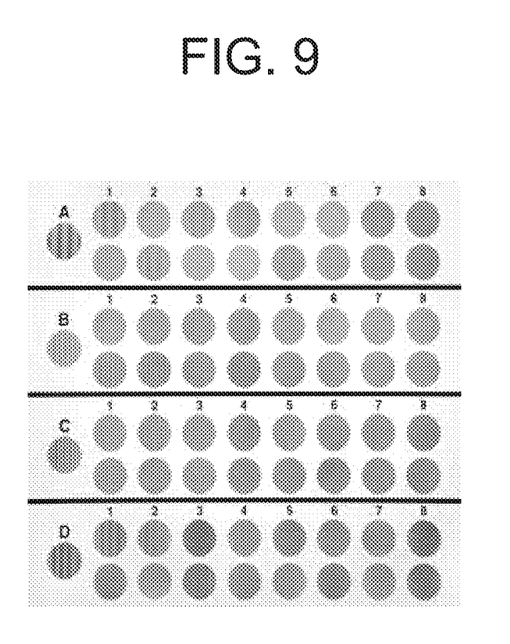
FIG. 9 is a representation of an alternate contrast sensitivity function test chart.

It is important to note that other test chart types may be utilized. FIG. 9 illustrates one such chart. In the chart of FIG. 9, a series of pairs of targets are presented to the patient. One contains the pattern and the other is blank. The patient must select the target with the pattern. These may be displayed side-by-side so that once again a left-right choice is required.

In accordance with another more preferred exemplary embodiment, the present invention utilizes the speed and efficiency of a computerized video system to fully implement a tilted-grating, forced choice test. A large number of test patterns based on Campbell-Robson charts may be generated and stored in the memory of a computer system. It is important to note that any suitable computer or computing system with sufficient memory and speed may be utilized to implement the present invention, including hand held devices. Each test pattern includes a patch with a sinusoidal pattern of a single spatial frequency with some level of contrast. The pattern is either tilted to the right, tilted to the left of not tilted at all, i.e. vertical. In a preferred exemplary embodiment, there may only be two choices (tilted left or tilted right), which may prove to be more beneficial than a three choice test as it greatly simplifies the response needed from the subject or patient. The patterns are presented one at a time to the subject or patient on a high resolution display, preferably 10 bit depth or greater, at a prescribed viewing distance. The patient will then have two or three buttons to push; namely, one corresponding to each orientation, and must provide a response, even if it is a guess. Once a button is pushed, a different pattern is presented. It is important to note that the buttons can be part of the user interface or simply part of a touch screen display. In addition, only two views may be presented, left or right leaning, rather than three choices, thereby speeding up the test and making it more accurate as explained above. In either example, the buttons may be color coated and feedback provided for ease of use and to make the test more interesting. Each time a button is selected, the next chart or image of the chart is presented. As before, the monitor should preferably be shielded to prevent ambient light from influencing the measurements by control of the test environment or other suitable means such as being enclosed in a box. The subject or patient views the monitor at a prescribed test distance, or alternatively, a viewing system comprising two eyepieces may be utilized to image the monitor to the desired viewing distance for the subject or patient. The spatial frequencies of the patterns may be adjusted for different viewing distances so that they correspond to the desired angular resolution.

In this exemplary embodiment, the computer will record each response and advance the patient to the next pattern. There is no need for a clinician to record the response or point to the next pattern. All of the patterns are presented in the same position on the monitor thereby removing any potential variation. The patterns may be presented in a random order thereby preventing any learning influences. Finally, the computer system generates the CSF response for the subject.

The computer automated system offers a number of advantages in addition to the automatic recording of responses and speed. A large number of different patterns may be generated to provide for additional accuracy. For example, additional patterns near the contrast threshold may be displayed. In other words, smaller increments in the properties of the patterns may be utilized to get the subject or patient closer to his or her threshold. In a similar manner, the test may be adjusted dynamically based upon the subject's or patient's response and areas of particular interest may be more fully explored. In addition, while exploring these areas of interest at or near the contrast limit or threshold, easy to identify patterns may be inserted into the test to maintain the subject's or the patient's level of interest in the test. A synchronized audio clue may be provided to alert the subject or patient when a new pattern is displayed. The audio feedback may be modified on a correct or incorrect response. Alternatively, a video clue, for example, a smiley face, a green check, fireworks or something similar may be utilized and may be particularly helpful with children of all ages. Any video clue utilized is preferably chosen so as to not distract the subject or patient away from the task or to introduce any accommodation or adaptation into the visual system. A key benefit is getting to test more frequencies in children by both making the test faster and more entertaining. In addition, a larger number of spatial frequencies may be measured. Variations of the testing procedure are easy to implement, for example, testing speed may be increased if only left and right tilts are utilized rather that left, right and vertical as set forth above.

In one exemplary embodiment, the testing process may be divided into N spatial frequency ranges and repeated M times per range to produce an average CSF. The order of frequencies should preferably be random and an averaging algorithm should be implemented to detect recency bias to prevent learning influences.

It is expected that a subject or patient should be able to view and respond to the pattern within a few seconds with the computerized system of the present invention. It is possible that the subjects or patients be forced to respond within a certain time period. Accordingly, within five minutes of testing, approximately one hundred (100) or more different patterns may be evaluated.

Utilizing a computerized, high bit depth video display system will provide an accurate, flexible method for measuring the human visual contrast sensitivity function while making use of the desired true forced choice methods and eliminating the issue of subject fatigue.

Figure 8:
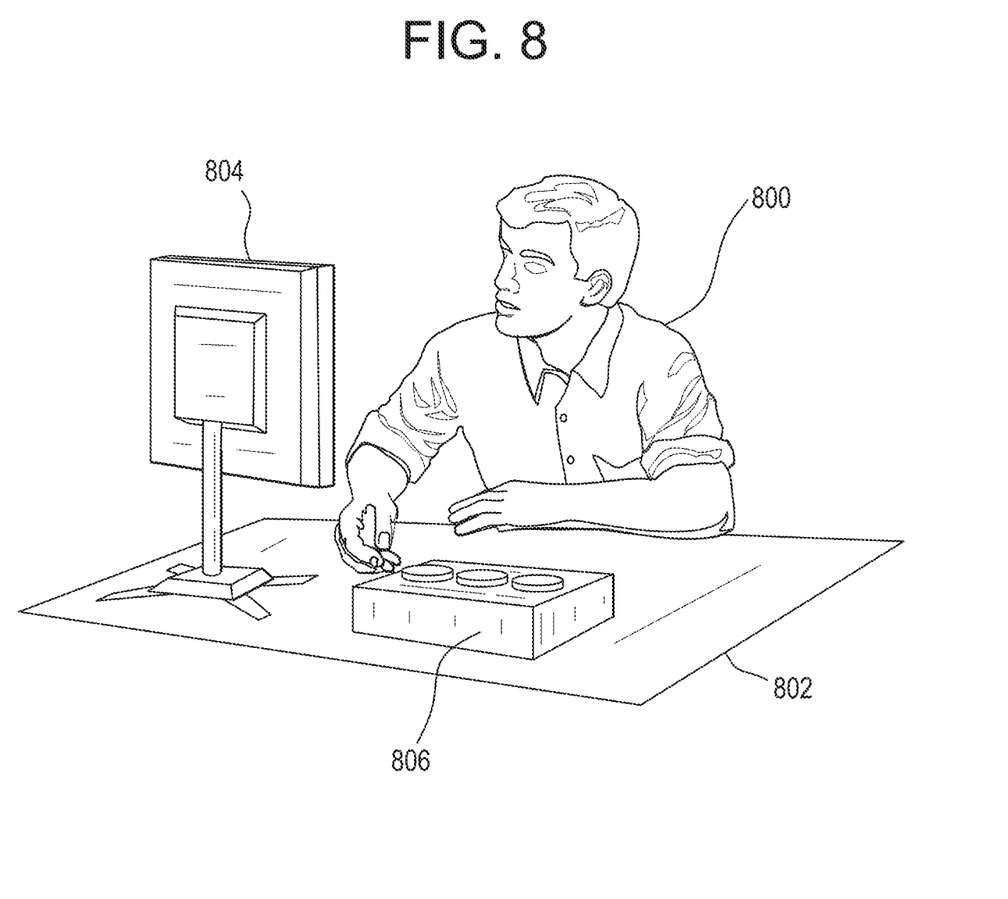
FIG. 8 is a diagrammatic representation of a patient engaged in a visual contrast sensitivity function test in accordance with the present invention.

Referring now to FIG. 8, there is illustrated an subject/patient 800 seated at a table 802 engaged in a visual contrast sensitivity function test. As described above, the subject/patient 800 views images presented on a high resolution monitor 804 positioned a predetermined distance for the individual 800, and utilize a patient interface 806 to indicate his or her answers. In this figure, the patient interface 806 is simply a device with three buttons; however, in other embodiments, any suitable device may be utilized for patient answer selection, including one with less buttons. For example, a touch screen application may be utilized. Alternately, a wired or wireless device, for example, a game-like console with a joystick may be utilized.

As briefly alluded to above, presenting the patterns is a video mode should preferably make the test more interesting for the patient 800. In this same vein, it may be beneficial to provide the patient 800 with feedback during the testing, for example different sounds for correct or incorrect answers, as this feedback may make the test more like a game making the test more interesting and arousing the individual's competitive nature with the added benefit of reducing the possibility of just guessing, for example, tilted right every time the patient 800 cannot see the pattern.

In an alternate exemplary embodiment, the test patterns may be made to move on the monitor. In other words, rather than simply presenting the pattern as a static image on one part of the monitor, the patterns may be programmed to move around the screen in a random pattern so that the subject or patient first has to track and capture the image before making his or her choice. This "hunting" feature may extend the testing time allocated to children as their attention is kept longer with more developed gaming. This is important in the testing of myopia correction devices. While this is not a pure CSF test, it may be utilized or tailored to a visual function test. As long as the monitor has the required resolution and consistent intensity, there should be no problem associated with moving the image around.

In addition, as the test is implemented on a computer the time between the presentation of a new image or pattern and the subject or patient response may be recorded. The time to decision may be collected and utilized. More specifically, the timing information may be utilized to make the test more accurate. For example, a quick response should mean that the patient found sufficient contrast to make the decision quickly, whereas a long delay may mean the patient is having difficulty with the pattern and that the contrast of the pattern is at or near the contrast limit. In other words, time may be another factor in zeroing in on the threshold. More specifically, time should be factored into developing an adaptive algorithm that is part of the test designed to find thresholds. Essentially, the time to response should be inversely related to the certainty of the response.

Time may also be utilized to predict binocular performance when the times for consistent intensity frequencies or patterns are compared as ratios between the two eyes. The greater the ratio is from unity, the less ability to have binocular summation. This is important in the development of lenses for correcting presbyopia.

Once the test is complete, a qualitative result is produced and utilized as described herein. The application of the present invention to contact lens design and evaluation is significant. A patient may be fitted with a set of contact lenses and the contrast sensitivity function testing of the present invention performed. Not only will the clinician find out if the patient likes the contact lenses or not, but quantitative information about the lens performance on the eye is obtained quickly. Accordingly, different lenses may be evaluated for patient satisfaction along with quantitative CSF data for each. It may be determined that there is/are a specific spatial frequency or frequencies that are crucial for patient satisfaction. The lens design can optimize this response at the expense of other less important spatial frequencies.

Figure 10:
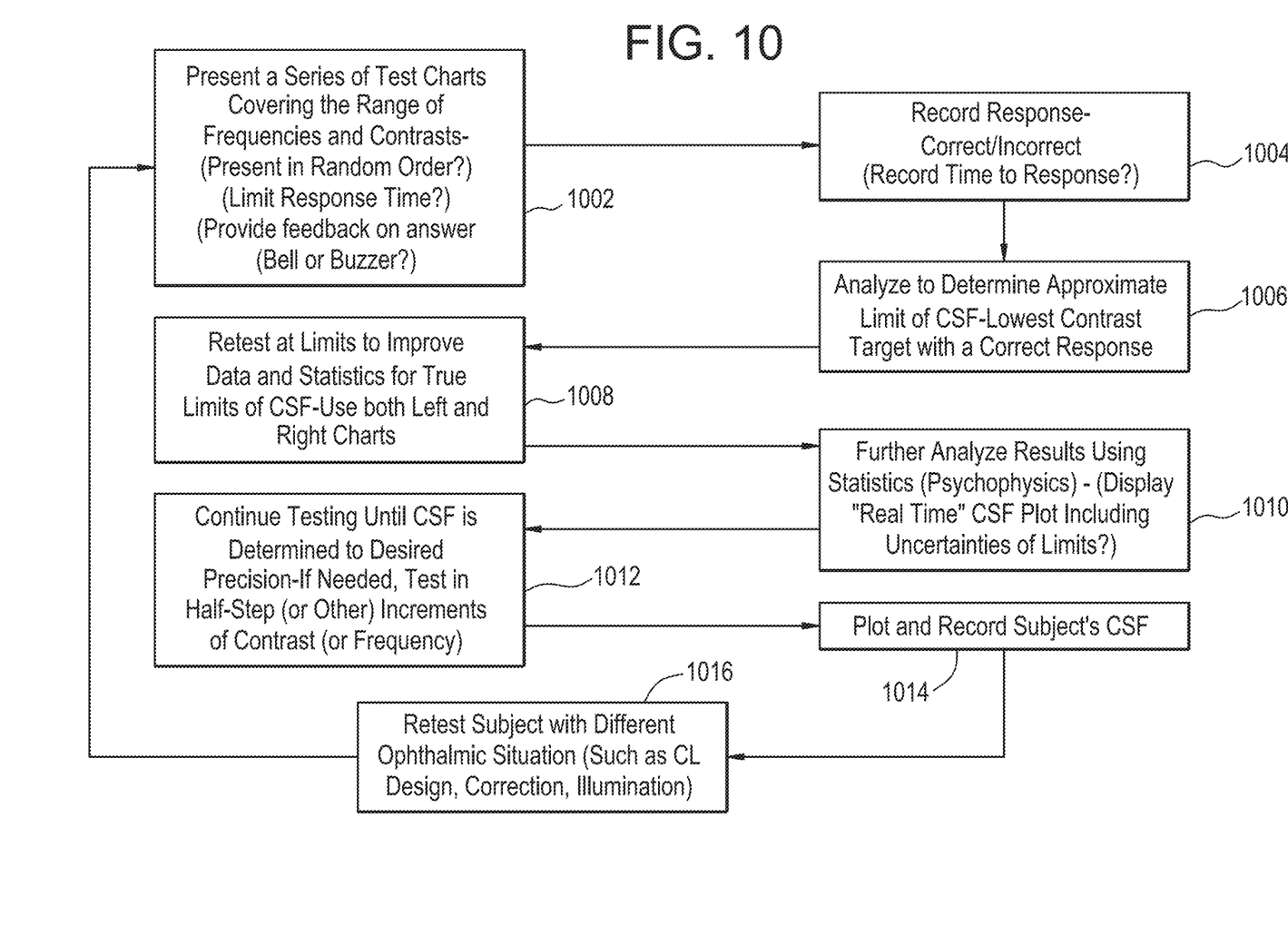
FIG. 10 is a flow chart of a process to perform a visual contrast sensitivity function test in accordance with the present invention.

FIG. 10 illustrates a flow chart of the basic structure of a process utilized in accordance with the present invention. In the first step, 1002, the subject or patient is presented with a series of test charts covering a range of frequencies and contrasts. As set forth above, the first step may include the pre-testing with a Campbell-Robson test chart or any other suitable chart. In addition, as set forth herein, the test charts may be in random order, the response time limited or recorded, and feedback provided, all as discussed in detail above. In the next step, 1004, the subject's or patient's response is recorded as well as the time to choose a response. In the next step, 1006, the responses are analyzed to determine to determine an approximate limit of CSF, basically, the lowest contrast target with a correct response. In the next step, 1008, the subject or patient may be retested at the limit to improve data and statistics for the true limit of CSF. In the next step, 1010, the results of the retesting are further analyzed utilizing statistical methods (pyschophysics). In addition, a real time CSF plot may be displayed for inspection. In the next step, 1012, testing is continued until the CSF is determined to the desired precision. As set forth herein, half-steps or any other incremental steps may be utilized to zero-in on an accurate CSF. In the next step, 1014, the subject's or patient's CSF is plotted and recorded. In the last step, 1016, the subject or patient may be re-tested with a different ophthalmic solution, for example, a different spectacle or contact lens. It is important to note that variations in the process may be utilized. In addition, as set forth above, any suitable computer or computer system with the required speed and memory capacity may be utilized to implement the process of the present invention.

It is important to note that the patient feedback mechanism may comprise a single button and a continuous feedback knob or slider. The patient sets the knob based on their confidence in selecting the correct forced choice. The continuous response is fed into the adaptive algorithm in a similar fashion as time as discussed above. The confidence from the patient allows the adaptive algorithm to more quickly hone in on the threshold. In addition, the gaming aspect of the present invention, including the video and feedback is an important aspect of the invention as it serves to better engage the patient.

Although shown and described in what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. A method for implementing a tilted-grating, forced choice contrast sensitivity function test, the method comprising the steps of:

presenting a patient with a first series of randomized test chart sets with two or more choices per set on a high resolution display as a video and covering a first range of frequencies and contrasts;

having the patient select a response from the two or more choices, recording if the response is correct or incorrect, recording the time the patient utilized in making the response, and providing the patient with additional choices until the first series of test charts are complete;

analyzing the responses to determine a first contrast sensitivity function;

presenting the patient with additional series of randomized test chart sets with two or more choices per set on a high resolution display as a video and covering a at least one of a second range of frequencies and contrasts in smaller increments than the first range of frequencies and contrasts, a change in spatial frequencies, a change in contrast, a change in spatial frequencies and contrast and continue until a contrast sensitivity function is generated to a desired precision;

having the patient select a response from the two or more choices, recording if the response is correct or incorrect, recording the time the patient utilized in making the response, and providing the patient with additional choices until the second series of test charts are complete;

analyzing the responses utilizing statistical methods;

repeating the method until a desired ophthalmic resolution is obtained as determined by an adaptive algorithm; and storing and plotting the contrast sensitivity function to provide an accurate quantitative result for the contrast sensitivity function.

2. The method for implementing a titled-grating, forced choice contrast sensitivity function test according to claim 1, wherein the step of presenting a patient with a first series of randomized test chart sets and presenting the patient with additional series of randomized test chart sets includes presenting them one at a time at a prescribed viewing distance.

3. The method for implementing a titled-grating, forced choice contrast sensitivity function test according to claim 1, further comprising a synchronized audio clue when a new chart set is presented.

4. The method for implementing a titled-grating, forced choice contrast sensitivity function test according to claim 1, further comprising visual feedback upon receipt of a response by the patient in order to maintain the interest of the patient.

5. The method for implementing a titled-grating, forced choice contrast sensitivity function test according to claim 1, further comprising introducing gaming features to maintain the interest of the patient.

6. The method for implementing a titled-grating, forced choice contrast sensitivity function test according to claim 1, further comprising utilizing the time to response as part of an adaptive algorithm to find contrast thresholds.

7. The method for implementing a titled-grating, forced choice contrast sensitivity function test according to claim 1, wherein the step of repeating the method until a desired ophthalmic solution is obtained includes fitting the patient with a lens design that optimizes performance and comfort for the patient.

* * * * *